United States Patent
Heermann

(10) Patent No.: US 6,403,038 B1
(45) Date of Patent: Jun. 11, 2002

(54) MAGNETIC PIN FOR CONCENTRATING AND SEPARATING PARTICLES

(76) Inventor: Klaus-Hinrich Heermann, Max-Born-Ring 47, 37077 Göttingen (DE)

(*) Notice: Subject to any disclaimer, the term of this patent is extended or adjusted under 35 U.S.C. 154(b) by 0 days.

(21) Appl. No.: 09/463,057

(22) PCT Filed: Jul. 15, 1998

(86) PCT No.: PCT/DE98/02014

§ 371 (c)(1),
(2), (4) Date: Apr. 3, 2000

(87) PCT Pub. No.: WO99/04239

PCT Pub. Date: Jan. 28, 1999

(51) Int. Cl.[7] ............................................. B01L 11/00
(52) U.S. Cl. ................... 422/101; 422/100; 422/102; 422/50; 422/99; 294/65.5; 210/695; 335/285
(58) Field of Search ........................ 422/100, 101, 422/99, 65, 50; 435/287.1; 210/425, 695; 294/65.5; 424/1.29; 436/177; 335/285

(56) References Cited

U.S. PATENT DOCUMENTS

| | | | |
|---|---|---|---|
| 512,381 A | * 1/1894 | Keyes | 294/65.5 |
| 2,372,930 A | * 4/1945 | Bovee | 145/61 |
| 2,417,762 A | 3/1947 | Koller | |
| 2,471,764 A | * 5/1949 | Miller et al. | 294/65.5 |
| 2,547,990 A | * 4/1951 | Willms | 294/65.5 |
| 2,693,979 A | * 11/1954 | Russell | 294/65.5 |
| 2,993,723 A | * 7/1961 | Twachtman et al. | 294/65.5 |
| 3,169,791 A | * 2/1965 | Twachtman | 294/65.5 |
| 3,789,336 A | * 1/1974 | Gordin | 335/285 |
| 3,826,619 A | * 7/1974 | Bratu, Jr. et al. | 23/253 R |
| 3,867,517 A | * 2/1975 | Ling | 424/1 |
| 3,981,776 A | * 9/1976 | Saxholm | 195/103.5 R |
| 3,985,649 A | * 10/1976 | Eddelman | 210/42 S |
| 4,272,510 A | * 6/1981 | Smith et al. | 427/47 |
| 4,649,116 A | * 3/1987 | Daty et al. | 435/287 |
| 5,169,193 A | * 12/1992 | Stelmach | 294/65.5 |
| 5,265,887 A | * 11/1993 | Stelmach | 294/65.5 |
| 5,288,119 A | * 2/1994 | Crawdord, Jr. et al. | 294/65.5 |
| 5,525,302 A | * 6/1996 | Astle | 422/100 |
| 5,582,796 A | * 12/1996 | Carey et al. | 422/65 |
| 5,647,994 A | * 7/1997 | Tuunanen et al. | 210/695 |
| 5,942,124 A | * 8/1999 | Tuunanen | 210/695 |
| 6,024,925 A | * 2/2000 | Little et al. | 422/100 |
| 6,040,192 A | * 3/2000 | Tuunanen | 436/177 |
| 6,056,339 A | * 5/2000 | Berger | 294/65.5 |
| 6,123,902 A | * 9/2000 | Koch et al. | 422/50 |

FOREIGN PATENT DOCUMENTS

| | | |
|---|---|---|
| JP | 09 304385 | 11/1997 |
| WO | WO87/05536 | 9/1987 |
| WO | WO94/18565 | 8/1994 |
| WO | WO96/12959 | 5/1996 |

OTHER PUBLICATIONS

Sargent–Welch Scientific Co. catalog (1984). p. 1265.*
Aldrich Chemical Company, Inc. catalog (1988). p. 2098.*

* cited by examiner

*Primary Examiner*—Jill Warden
*Assistant Examiner*—Brian J. Sines
(74) *Attorney, Agent, or Firm*—Albert P. Halluin; Viola T. Kung; Howrey Simon Arnold & White, LLP

(57) ABSTRACT

The invention relates to a magnetic pin (8, 22) for concentrating particles, containing
(a) a grip adapter (2, 14),
(b) a connecting pin (4, 16) with dents (3, 15),
(c) at least one magnet (7, 20) and
(d) a sheath (5, 18).

11 Claims, 3 Drawing Sheets

MAGNETIC PIN FOR CONCENTRATING AND SEPARATING PARTICLES

Figure 1A:
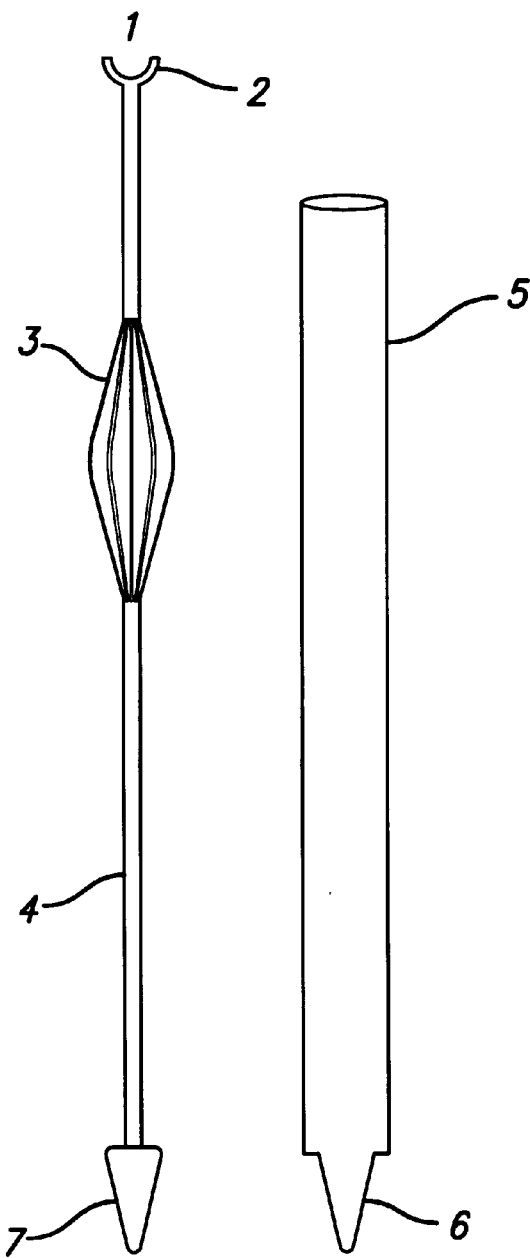

The present invention relates to a magnetic pin for concentrating and separating particles.

The latest detection methods for nucleic acids, such as polymerase chain reaction (PCR), ligase chain reaction (LCR), nucleic acid sequence based amplification (NASBA), strand displacement amplification (SDA), can be carried out by amplification of nucleic acids with extreme sensitivity. Because of this sensitivity the methods are very susceptible to contaminations. In this connection, the danger of contamination increases with the increasing number of steps and the manipulations to be made, such as centrifugation and pipetting steps. Thus, it should be important to the experimenters to keep the number of steps and manipulations as small as possible. However, this is often problematic, since differing sample volumes must be observed for differing steps and concentration of the sample volume is necessary in between. Therefore, there is a demand for a possibility of dispensing with manipulation steps, particularly centrifugation steps, in the above mentioned method, by taking the sample to be analyzed directly out of the various vessels, such as cups or microtiter trays, and transferring it. This demand of easily transferring samples from a large volume to a smaller volume and being able to easily change the sample containers, respectively, is, of course, not only limited to the field of nucleic acid technique but exists throughout (bio)chemistry where the concentration of samples is necessary.

Therefore, it is the object of the present invention to provide an apparatus by means of which target molecules can easily be taken out of the containers or vessels and transferred into other vessels so as to be able to dispense with manipulation steps, such as centrifugation steps, and work with small volumes.

This object is achieved by a magnetic pin according to claim 1. Advantageous embodiments follow from the subclaims.

In order to derive an advantage for the above mentioned methods by means of the magnetic pin according to the invention, magnetic labeling of the target molecules must, of course, be given. A person skilled in the art knows how to achieve this. For example, this is achieved in that the target molecules as such have magnetic properties or are bound to "magnetic beads". If a detection method is concerned, another possibility is to link streptavidin to iron so as to bind the target molecules which in turn are labeled with biotin.

In an exemplary method in which the magnetic pin according to the invention is used, the sample material, e.g. serum, plasma, whole blood, cells or tissue, is subjected to a chemical or chemico-enzymatic breaking-up and a denaturation, respectively. This solution simultaneously contains a first nucleic acid oligonucleotide (primer) which hybridizes as a probe to the target molecules. This oligonucleotide is covalently bonded to a biotin molecule which can be bound by streptavidin with high affinity. This streptavidin in turn is bound to particles which contain iron. Because the streptavidin particles cannot be added to a denatured sample mixture, since otherwise they would denature as well and would lose their bonding properties to biotin, the sample mixture must be diluted, which increases the sample volume. However, this great sample volume has a negative effect on subsequent steps, such as amplifications. For example, the resulting conjugates (sample—oligonucleotide—biotin—streptavidin—iron) are transferred by means of the magnetic pin according to the invention into another container where the further steps can then take place in a much smaller volume.

Figure 1B:
Figure 2:
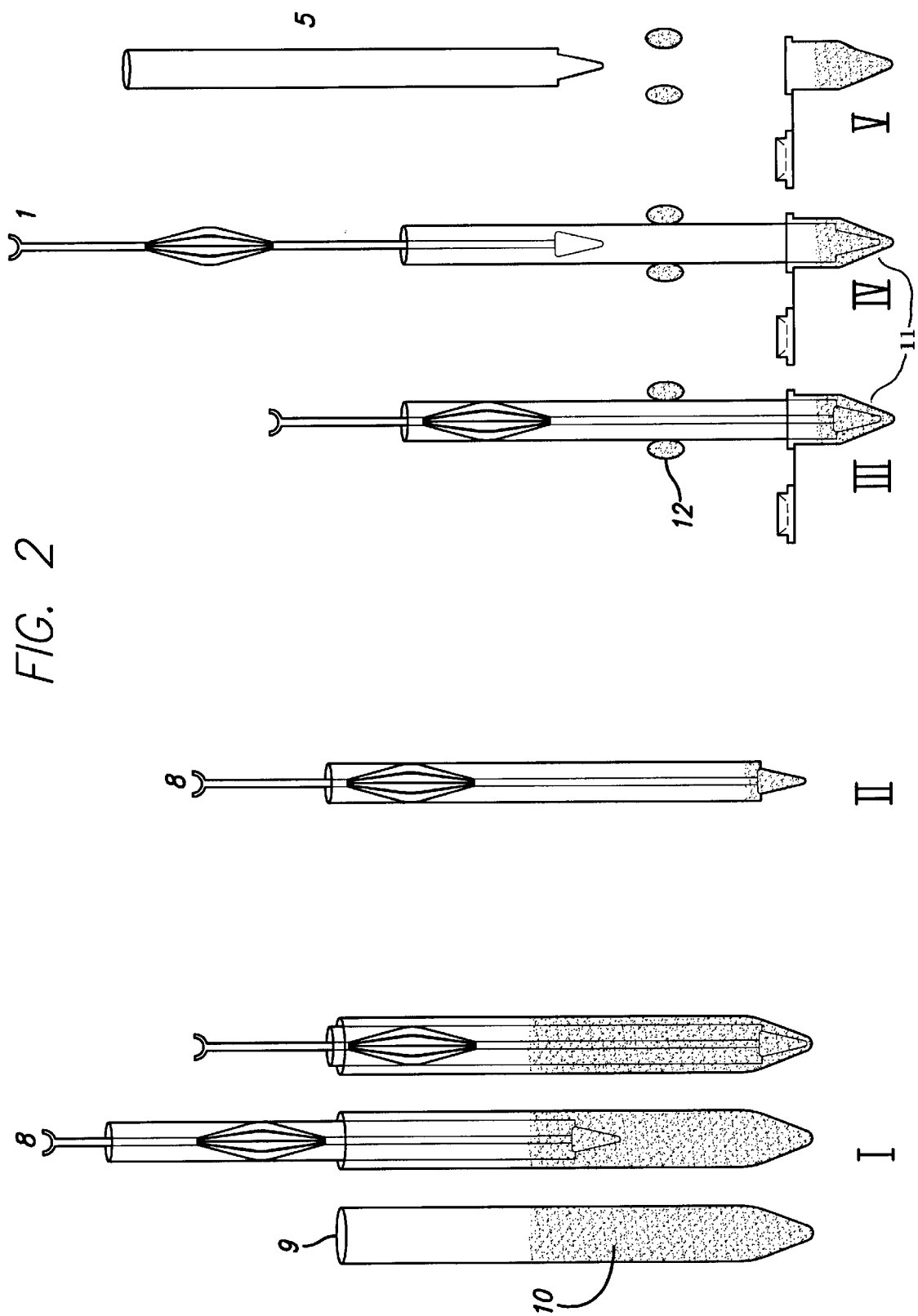
Figure 3A:
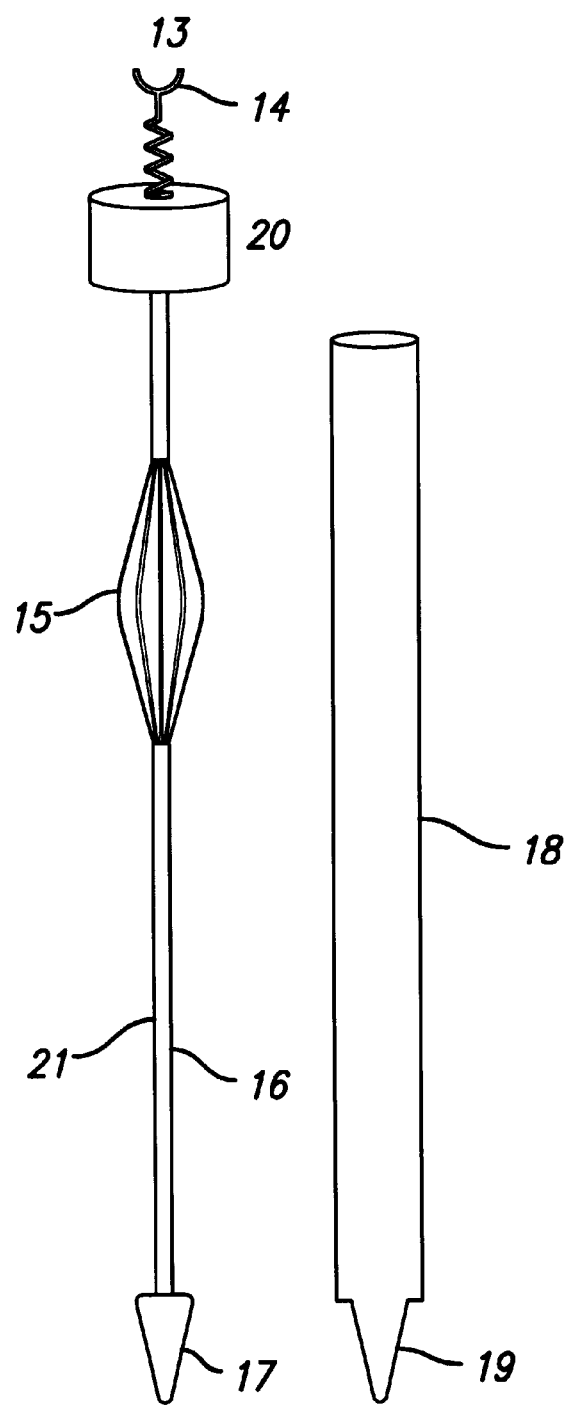
Figure 3B:
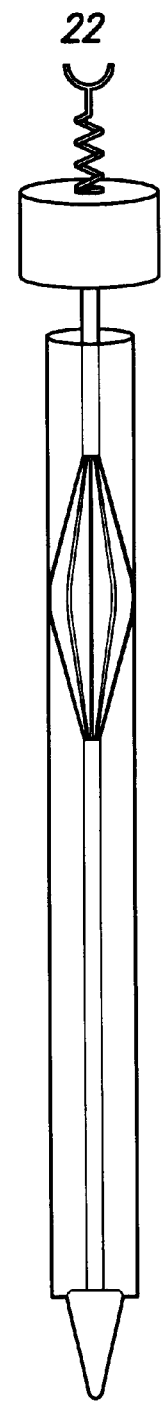

The invention is further described by means of the figures in which:

FIG. 1a shows individual components of a magnetic pin 8 according to the invention, FIG. 1b shows the assembled magnetic pin 8 according to the invention, FIG. 2 shows the transfer of particles from a large sample container into a small sample container, FIG. 3a shows individual components of another magnetic pin 22 according to the invention, FIG. 3b shows the assembled magnetic pin 22 according to the invention.

The individual components of an embodiment of a magnetic pin according to the invention are shown in FIG. 1a. The magnetic pin 1 has a grip adapter 2 at its rear end. It is developed such that it can be gripped and operated by an industrial automatic pipetting machine. Here, the grip adapter 2 is preferably made of a deformable material, such as rubber. In addition, the magnetic pin 1 comprises a connecting pin 4 having a dent 3 so as to form a grip for the automatic pipetting machine. Furthermore, the dent serves for holding a sheath 5. This sheath 5 is thin-walled (wall thickness about 0.2 to 0.7 mm, preferably 0.3 mm) and consists preferably of polymeric plastics (e.g. polypropylene) and a non-magnetizable, but conductive, material, respectively, e.g. plastics having a graphite portion. The sheath 5 has preferably a conical shape at its lower end and has a constriction 6, which is preferably adapted to sample containers such that with a small liquid volume (e.g. 25 μl in a PCR cup) it is just wet in a filled sample container. The connecting pin 4 should be made of a non-magnetic material, such as aluminum. The front end of the magnetic pin has a magnetic head 7 which has preferably a conical shape. Every conventional permanent magnet is in consideration for this.

FIG. 1b shows a magnetic pin 1 provided with the sheath 5 as the magnetic pin 8 according to the invention.

The concentration of the magnetically labeled sample material present in the sample containers is preferably carried out with the magnetic pin 8 disposed in the sheath and preferably proceeds as shown in FIG. 2.

I) The magnetic pin with the sheath 8 is immersed in a large sample container 9 including magnetically labeled particles 10 disposed in a liquid. Pin and sheath are slowly moved downwards. The particles are attracted by the magnetic head of the magnetic pin.

II) The magnetic pin with sheath 8 is slowly drawn out of the sample container again, so that only minor liquid residues adhere to the sheath. The adhering particles can optionally be subjected to further treatments in a wash vessel without a loss of the adhering particles occurring.

III) The tip of the magnetic pin including the sheath surrounding it are immersed in a smaller sample container 11. Because of the adaptation of the magnetic head 7 including the surrounding sheath to the shape of the sample container, only a small liquid volume is required to wet the sheath of the entire tip. The sheath is fixed in stand or support 12.

IV) The magnetic pin 1 is drawn out of the sheath by a rapid movement. The particles separate, in the model case, from the sheath because of the omitted magnetic force and stay in the sample container 11. Should this not suffice, they will be pulled downwards by another magnet located externally underneath the sample container.

V) The sheath 5 is carefully removed from the sample container 11.

Result: The particles are now found in a smaller volume in another sample container.

Another preferred embodiment of a magnetic pin according to the invention is shown in FIG. 3. The individual components of such a magnetic pin are shown in FIG. 3*a*. As in FIG. 1, the magnetic pin comprises a grip adapter 14, a dent 15, a connecting pin 16, a sheath 18 and a constriction 19. The above-mentioned product and dimensional parameters for these components also apply to the embodiment according to FIG. 3. In the embodiment shown in FIG. 3 the magnetic forces, which shall escape the tip 17 in beamed fashion, emanate from a relatively great permanent magnet 20 which is mounted farther above, and are directed e.g. by an iron core to the tip 17. In this case, the magnetic field directly emanating from the magnet can be shielded by a metallic sheath 21, such as an iron sheath. The magnet 20 can be disposed at any height on the connecting pin 16. However, it is preferably found near the grip adapter, since it can have a disturbing effect if located farther downwards when the magnetic pin is immersed in a sample container. The tip 17 consists of a magnetizable material and can have magnetic properties itself, respectively, i.e. can be the continuation of the iron core.

FIG. 3*b* shows a magnetic pin 13 provided with a sheath 18 as the magnetic pin 22 according to the invention.

According to the invention, the magnetic force shall effect the separation of target substances through the help of other suitable substances. Therefore, it is not the magnet as such that is decisive but its shape and its arrangement. The shape of the magnet influences decisively the course of the magnetic field and thus its force, on the one hand, and the shaping must be accurately in conformity with the target application in this case, on the other hand. In a preferred embodiment, the collection of magnetic particles from solutions (such as serum) takes place on the smallest possible area (tip of the magnetic pin). In this case, the magnetic force shall be as high as possible, so that the magnetic particles can be collected over a suitable container cross-section. Additional collection of the magnetic particles from a substantially greater starting volume becomes possible by slowly lowering the magnetic pin within the container (e.g. serum tube). In addition, the shape of the magnetic tip must be adapted to the fact that when the magnetic pin is withdrawn the least possible liquid adheres thereto. At the same time, it must be taken into consideration in connection with the tip shape that when the pin is immersed in solutions, not even minute parts of this solution (droplets, aerosols) may pass into the air. In the final analysis, the shape of the pin must also be adapted to the target vessel, so that it suffices to supply the least possible liquid volume there to fully wet the site of the adhering magnetic particles. The object of the plastic sheath of the magnetic pin, which is part of the patent, is at this time to enable the stopping of the magnetic force. In order to achieve this objective, the magnetic pin is smartly drawn out of the sheath, whereupon the magnetic particles fall off the outside of the sheath.

Thus, the embodiment according to the present invention, which has a pointed shape of the magnet, offers special advantages when withdrawn from a solution. This process can also be automatically controlled temporally via a measurement of the induction when conductive sheaths are used, such that no drop is left at the tip withdrawn from the liquid surface. The starting solution has maximum reduction (single-step concentration). This is an important detail not only for the prevention of contamination dangers while moving over other samples but also for the separation and concentration of magnetic particles which is not possible in this way when a flat tip is used. Furthermore, the magnetic field has transverse orientation when the magnet has a pointed shape, so that an improved collective effect occurs.

As a result, the magnetic particles can be supplied in an extremely small liquid volume by a pointed shape which has to be adapted to the employed containers. If a corresponding vessel is used on the receiving side, a magnetic tip can also be used for transferring substances and removing impurities by washing from a very small starting volume.

Another advantage of the magnetic pin according to the invention is that the target molecules of the sample are easily concentrated and separated. Furthermore, this is inexpensive, since the sheath is made of cheap material and can be discarded and rinsed, respectively, whereas the actual magnetic pin has a long service life and can be used again without further purification, since in the model case it is not in contact with the sample.

What is claimed is:

1. Magnetic pin (8, 22) for concentrating particles, comprising:

a connecting pin (4, 16) comprising a rear end and a front end (7, 17) and being provided with a dent (3, 15);

at least one magnet (7, 20) which is arranged at the connecting pin (4, 16), such that a magnetic filed emanates in concentrated fashion at the front end (7, 17); and a sheath (5, 18) into which the connecting pin (4, 16) can be introduced, which has a conical shape at its lower end, and consists of polymeric plastics and a non-magnetizable, conductive material;

wherein a grip adapter (2, 14) is arranged which serves for operating the magnetic pin (8, 22) through an automatic pipetting machine;

the front end of the connecting pin (4, 16) is provided with a magnetic head (7) which has a conical shape; and the sheath is moved in associated manner or separately from the connecting pin.

2. The magnetic pin according to claim 1, wherein the grip adapter (2, 14) is made of a deformable material.

3. The magnetic pin according to claim 1 or 2, wherein the grip adapter (2, 14) is developed such that it can be gripped and operated by an industrial automatic pipetting machine.

4. The magnetic pin according to claim 1 or 2, wherein the connecting pin (4, 16) is made of a nonmagnetic material.

5. The magnetic pin according to claim 1 or 2, wherein the magnet (7, 20) is a permanent magnet.

6. The magnetic pin according to claim 1 or 2, wherein the sheath (5, 18) is made of a nonmagnetizable material.

7. The magnetic pin according to claim 1 or 2, wherein the sheath (5, 18) is made of polypropylene.

8. The magnetic pin according to claim 1 or 2, wherein the sheath (5, 18) has a wall thickness of 0.2 to 0.7 mm.

9. The magnetic pin according to claim 1 or 2, wherein the dent (3, 15) has a shape adapted for fixing the sheath (5, 18).

10. The magnetic pin according to claim 1, wherein the connecting pin at the front end comprises the at least one magnet as magnetic head.

11. The magnetic pin according to claim 1, wherein the front end is a tip and the connecting pin has a magnet whose magnetic forces emanate from the tip in beamed fashion.

* * * * *